United States Patent [19]

Archibald

[11] Patent Number: 4,585,441

[45] Date of Patent: Apr. 29, 1986

[54] IV FLUID CONTROL SYSTEM WITH FLUID RUNAWAY PREVENTION

[75] Inventor: G. Kent Archibald, White Bear Lake, Minn.

[73] Assignee: Minnesota Mining and Manufacturing Company, St. Paul, Minn.

[21] Appl. No.: 650,838

[22] Filed: Sep. 17, 1984

[51] Int. Cl.⁴ .............................................. A61M 5/00
[52] U.S. Cl. ..................................... 604/245; 604/65; 128/DIG. 12; 128/DIG. 13
[58] Field of Search ............... 128/DIG. 12, DIG. 13, 128/1 R; 604/245, 247, 65, 66, 67, 118

[56] References Cited
U.S. PATENT DOCUMENTS

| | | |
|---|---|---|
| 3,890,968 | 6/1975 | Pierce et al. ............ 128/DIG. 13 X |
| 4,094,318 | 6/1978 | Burke et al. ............ 128/DIG. 13 X |
| 4,210,138 | 7/1980 | Jess et al. ............... 128/DIG. 12 X |
| 4,217,993 | 8/1980 | Jess et al. ........................... 604/65 X |
| 4,460,358 | 7/1984 | Somerville et al. ........... 604/245 X |
| 4,496,351 | 1/1985 | Hillel et al. ....................... 604/65 X |

Primary Examiner—Edward M. Coven
Attorney, Agent, or Firm—Kinney & Lange

[57] ABSTRACT

An IV fluid control system having an IV set and a control device (such as an IV controller or fusion pump) includes a flow sensor which senses the flow of fluid through the IV set. Fluid runaway is prevented by an interlock which prevents removal of the IV set from the control device unless the fluid flow through the IV set is stopped. As a result, the medical personnel must clamp the outlet tubing of the IV set to stop fluid flow before removing the IV set from the control device.

15 Claims, 4 Drawing Figures

IV FLUID CONTROL SYSTEM WITH FLUID RUNAWAY PREVENTION

BACKGROUND OF THE INVENTION

1. Field of the Invention

The present invention relates to the administration of intravenous (IV) fluids. In particular, the present invention relates to an IV fluid control system which prevents fluid runaway when an IV set is being removed from the control device.

2. Description of the Prior Art

To improve health care, there has been considerable effort with regard to the administration of intravenous (IV) fluids. Both controllers and pumps have been developed for delivering metered amounts of IV fluid to the patient.

In both IV controller systems and IV infusion pump systems, a disposable IV set often is used which includes a chamber (or chambers), inlet tubing for connection to the source of fluid, and outlet tubing for connection to the patient. The chamber is inserted into the control device, which acts on the chamber to control the flow of IV fluid through the IV set.

It is desirable to have an IV control system in which fluid runaway is prevented when the IV set is removed from the control device. Prior art devices restrict flow when the set is removed from the control device and require complex and expensive the disposable IV sets.

SUMMARY OF THE INVENTION

The present invention is an improved IV control system which prevents fluid runaway when an IV set is removed from the control device. In the present invention, a sensor provides a sensor signal which is a function of a parameter which changes depending on whether or not the clamp is closed (i.e. whether fluid is flowing through the IV set). The invention further includes means responsive to the sensor signal for providing an indication that the IV set from the control device should not be removed unless the sensor signal indicates that fluid flow through the IV set is stopped.

The present invention, therefore, encourages the medical personnel to clamp off the outlet tubing of the IV set to stop fluid flow before the IV set can be removed from the control device. Once flow is stopped by the clamp, the IV set can be removed without danger of fluid runaway.

In some of the preferred embodiments, the control device includes a receptacle for receiving and holding the IV set when in operation, and a door which covers an opening to the receptacle. The means for providing an indication locks the door in a closed position as long as the sensor signal indicates a non-zero fluid flow. When the sensor signal indicates that fluid flow has stopped, the door is released, so that it can be opened and the IV set chamber can be removed from the control device.

In other embodiments, the sensor is a pressure sensor for sensing fluid pressure downstream from the portion of the IV set acted on by the control device. When the sensor indicates a pressure build-up (which results from clamping off of the outlet tubing), the door is released, so that it can be opened and the IV set can be removed from the control device.

In other preferred embodiments, the means for providing an indication produces a visual or audible warning (preferably in the form of a synthesized speech warning) when an attempt is made to remove the IV set if the clamp is not closed.

DETAILED DESCRIPTION OF THE PREFERRED EMBODIMENTS

Figure 1:
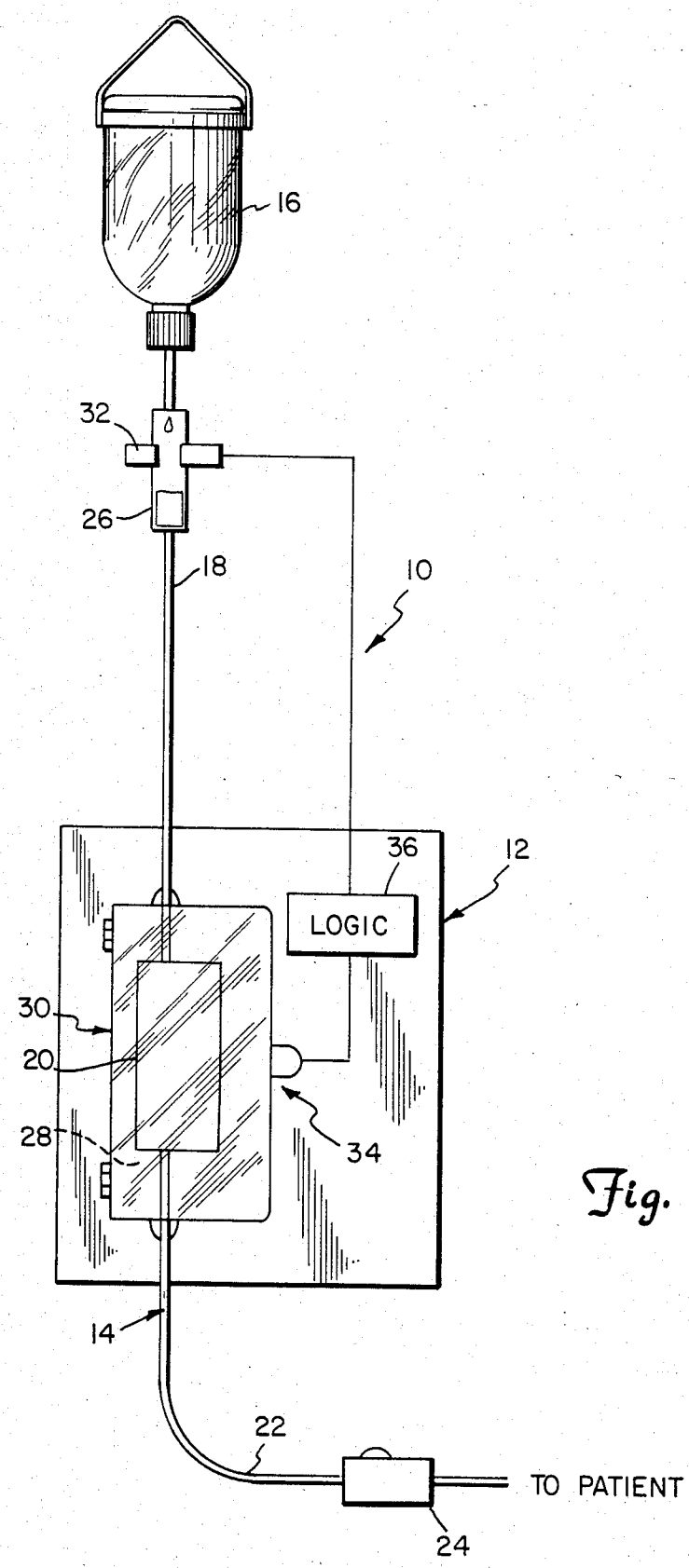
FIG. 1 is a schematic diagram of a first preferred embodiment of the IV fluid flow control system of the present invention.

In the preferred embodiment shown in FIG. 1, IV fluid flow control system 10 (which includes control device 12 and IV set 14) supplies IV fluid from fluid container 16 to a patient (not shown). Control device 12 is, in this embodiment, preferably an IV controller (although it can also be an IV infusion pump of a type which constantly is drawing fluid from container 16). IV set 14 includes inlet tubing 18, chamber 20, outlet tubing 22, and clamp 24. Fluid from IV fluid container 16 is supplied to inlet tubing 18 by means of drip chamber 26.

Chamber 20 of IV set 14 is inserted into receptacle 28 of control device 12. When in place within receptacle 28, chamber 20 is acted upon by the hardware of control device 12 so as to meter the amount of IV fluid being supplied to the patient. Chamber 20 will take a number of different forms, depending upon the specific arrangement of control device 12 and whether control device 12 is a pump or a controller.

As shown in FIG. 1, control device 12 includes door 30 which covers the opening of receptacle 28. Door 30 must be opened in order to insert chamber 20 into receptacle 28, and also must be opened in order to remove chamber 20 from receptacle 28.

The present invention is an improved system which prevents fluid runaway which could otherwise occur if the medical personnel failed to clamp outlet tubing 22 and then attempted to remove chamber 20 from control device 12.

In the embodiment shown in FIG. 1, the improvement of the present invention includes flow sensor 32, door lockout latch 34, and door interlock logic 36. Flow sensor 32 senses the flow of fluid through IV set 14, and provides a flow signal to interlock logic 36. As long as the sensed flow is non-zero, interlock logic 36 causes latch 34 to hold door 30 in a closed position. This prevents the medical personnel from removing chamber 20 from receptacle 28 so long as fluid is continuing to flow through IV set 14.

When the medical personnel closes clamp 24 to stop flow of fluid through IV set 14, the flow signal from flow sensor 32 changes, and interlock logic 36 releases door lockout latch 34. In other words, once clamp 24 has been closed, door 30 is released and chamber 20 can be removed from control device 12.

It can be seen that the present invention provides prevention of fluid runaway condition without adding any complexity to IV set 14. This provides a substantial cost advantage both to the manufacturer and to the user, since IV set 14 is a disposable item.

In the particular embodiment shown in FIG. 1, flow sensor 32 merely senses the drip rate in drip chamber 26 to provide an indication of flow rate. Other inexpensive flow rate sensors can also be used, since the precise accuracy of the flow rate is not essential to the present invention. In those systems which already include a flow sensor as part of the control system, the signal from that existing flow sensor can also be used to provide the fluid runaway prevention interlock of the present invention.

Similarly, the means for preventing removal of the chamber 20 from control device 12 preferably is extremely simple in construction. In the preferred embodiment shown in the Figure, door 30 and door lockout latch 34 are used because many control devices 12 currently in use already make use of a door to cover the chamber while control device 12 and IV set 14 are in use. The addition of a solenoid actuated latch, together with control logic for controlling operation of that solenoid latch as a function of flow signal, involves only a minor addition to the overall cost of control device 12.

Figure 2:
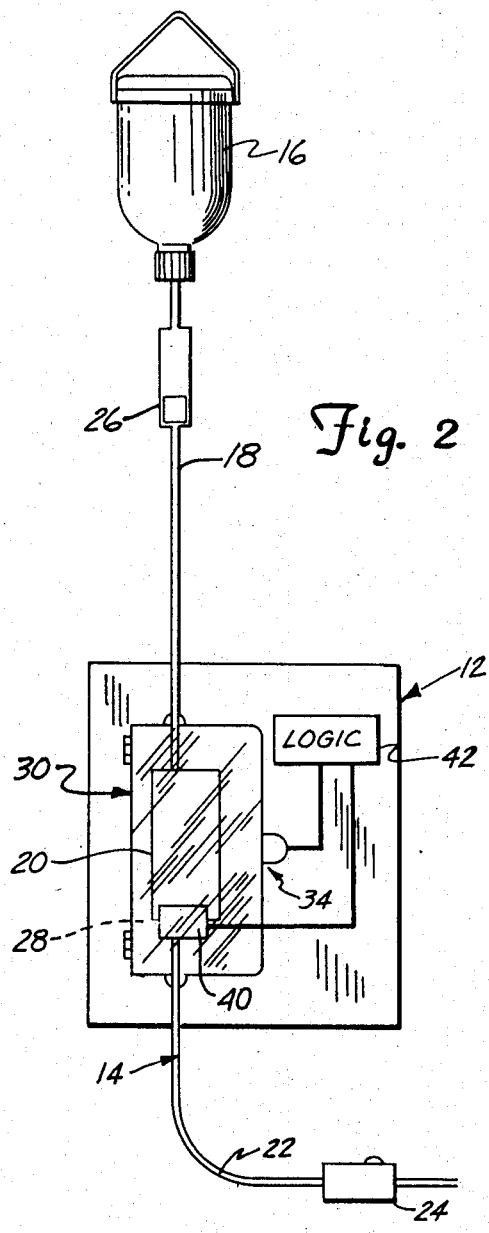
FIG. 2 is a schematic diagram of a second preferred embodiment of the IV fluid flow control system of the present invention.

FIG. 2 shows another embodiment of the present invention which is generally similar to the embodiment shown in FIG. 1, but which is particularly useful with IV pumps which have only fill (draw fluid from container 16) during part of each cycle. Similar elements, therefore, are designated with similar reference characters.

In the embodiment shown in FIG. 2, the parameter which is sensed is pressure at the outlet of control device 12, rather than fluid flow from fluid containers 16 to chamber 20 as in FIG. 1. Pressure sensor 40 is preferably located within control device 12, and senses outlet pressure at chamber 20. Interlock logic 42 responds to the pressure signal from pressure sensor 40, and only allows door lockout latch 34 to be released when the pressure is greater than a predetermined level.

The embodiment shown in FIG. 2 is particularly advantageous where control device 12 is a pump. When clamp 24 is closed and the pump is operating, there will be a pressure build-up in outlet tubing 22 which is sensed by pressure sensor 40. This pressure build-up is an indication that clamp 24 is closed, and therefore it is safe to open door 30.

Figure 3:
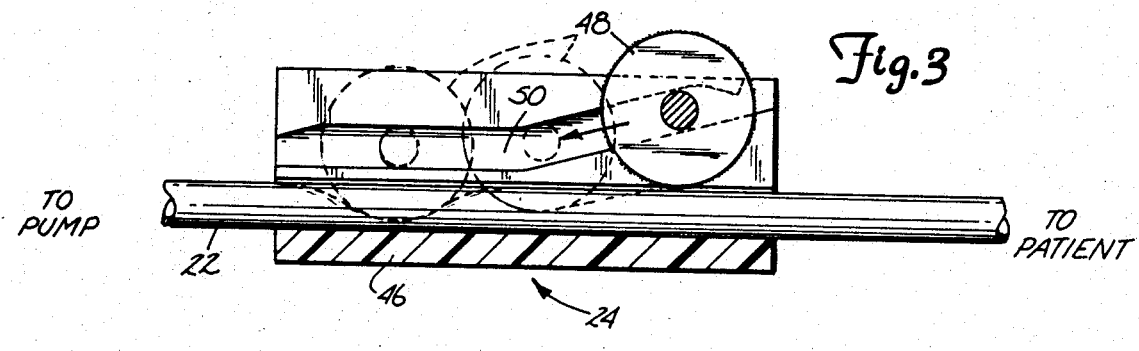
FIG. 3 is a partial sectional view of a clamp used in the system of FIG. 2.

If control device 12 is a pump and is pumping at very low flow rates, the compliance in outlet tubing 22 may cause a considerable delay before enough pressure is reached to signal logic 42 to allow door 30 to be opened. To avoid this potentially long delay while pressure is building up, clamp 24 is preferably a roller clamp having a housing 46 and a roller 48. The flow through outlet tubing 22 is constricted by moving roller 48 from right to left in FIG. 3. Because of guide track 50, roller 48 initially presses downward on tubing 22 to constrict flow as roller 48 is moved from right to left. As roller 48 continues to move to the left, it reduces the amount of volume of tubing 22 between clamp 24 and chamber 20, and therefore fluid is squeezed or forced back toward chamber 20 as clamp 24 is closed. This causes a pressure build up which is sensed by pressure sensor 40 and which provides the necessary signal to interlock logic 42 to release latch 34.

By using a roller clamp which causes a pressure increase, it is possible to release latch 34 even when control device 12 is in a stand-by mode (i.e. not pumping fluid).

Although in the embodiments shown in FIGS. 1 and 2, fluid flow and pressure have been used as the sensed parameters, other methods of sensing whether roller clamp 24 is closed can also be used in conjunction with the present invention. For example, in other embodiments ultrasonic sensing is used to sense whether clamp 24 is closed. In still other embodiments, an electromechanical switch indicates when clamp 24 has reached a fully clamped state.

Figure 4:
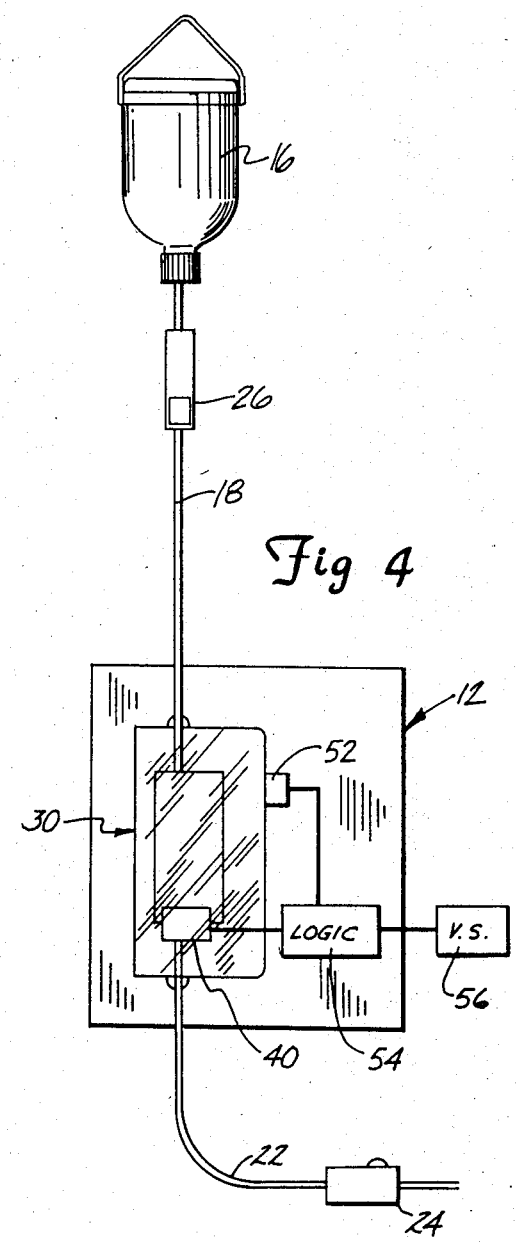
FIG. 4 is a schematic diagram of a third preferred embodiment of the IV fluid flow control system of the present invention.

FIG. 4 shows still another embodiment of the present invention which once again is generally similar to the system shown in FIGS. 1 and 2. Similar elements are designated by similar reference characters.

In the embodiment shown in FIG. 4, pressure sensor 40 provides a pressure signal, and door position sensor 52 provides a signal which indicates whether or not door 30 is closed. Both the door position signal and the pressure signal are provided to logic 54. When door 30 is opened (as indicated by the door position signal) and the pressure signal indicates that clamp 24 is closed, logic 54 takes no further action. If, on the other hand, the pressure signal indicates that clamp 24 is not closed and the door position signal indicates that door 30 is being opened, logic 54 actuates voice synthesizer 56, which provides an audible warning to the medical personnel that clamp 24 should be closed. This warning normally will be sufficient to prevent fluid runaway, because the medical personnel is immediately adjacent control device 12 at that time in order to open door 30.

Although the present invention also contemplates other types of annunciators other than voice synthesizer 56 (including visual or audio alarms), the synthesized speech provided by voice synthesizer 56 is preferred, since the hospital room commonly has a number of devices which can generate warning signals, and the synthesized speech provides a positive indication of the source of the alarm and the corrective action to be taken by the medical personnel.

The system of FIG. 4 is particularly advantageous for use with a control device 12 in which multiple steps must be performed by the medical personnel in a particular sequence in order to open door 30. When the first step of that multiple step process is performed (which for example may be the movement of a knob or lever), that step is sensed to indicate to logic 54 that door 30 is going to be opened (but has not yet been opened). This provides adequate time to provide a warning if clamp 24 is not closed.

In conclusion, the present invention is an extremely simple yet effective improvement for preventing fluid runaway in an IV fluid control system. The present invention avoids additional complexity in the disposable IV set and adds only a minimum amount of additional hardware to the control device.

Although the present invention has been described with reference to preferred embodiments, workers skilled in the art will recognize that changes may be made in form and detail without departing from the spirit and scope of the invention.

What is claimed is:

1. In an IV fluid control system of a type including an IV set for connection between a source of fluid and a patient, and a control device for receiving and acting upon a portion of the IV set to control fluid flow from the source to the patient; the improvement comprising:

means for providing a sensor signal which is a function of a parameter which changes depending on whether there is fluid flow through the IV set; and means responsive to the sensor signal for providing an indication that the IV set should not be removed from the control device unless the sensor signal indicates that fluid flow through the IV set is stopped.

2. The invention of claim 1 wherein the control device has a receptacle for receiving and holding a portion of the IV set when in operation, and wherein the means for providing an indication prevents removal of the IV set from the receptacle unless the sensor signal indicates that fluid flow through the IV set is stopped.

3. The invention of claim 2 wherein the means for providing an indication comprises:
   a door for covering the receptacle when in a closed position and having an open position in which the portion of the IV set can be inserted into or removed from the receptacle; and
   means for maintaining the door in its closed position when the sensor signal indicates non-zero fluid flow through the IV set and releasing the door to permit it to be moved to its open position when the sensor signal indicates that fluid flow to the IV set is stopped.

4. The invention of claim 1 wherein the means for providing a sensor signal comprises a flow sensor for sensing fluid flow through the IV set.

5. The invention of claim 1 wherein the means for providing a sensor signal comprises a pressure sensor for sensing fluid pressure in the IV set downstream from the portion of the IV set acted upon by the control device.

6. The invention of claim 5 and further comprising a clamp for selectively clamping a portion of the IV set at a position between the control device and the patient.

7. The invention of claim 6 wherein the clamp, as it is closed, acts on the IV set to produce a fluid pressure increase which is sensed by the pressure sensor.

8. The invention of claim 1 and further comprising:
   means for providing a signal indicating an attempt to remove the IV set from the control device; and wherein the means for providing an indication provides a human perceivable warning based upon the sensor signal and the signal indicating an attempt.

9. In an IV fluid control system of a type including an IV set for connection between a source of fluid and a patient, a control device for receiving and acting upon a portion of the IV set to control fluid flow from the source to the patient, and a clamp which is closable to clamp off fluid flow from the portion of the IV set acted upon to the patient; the improvement comprising:
   means for providing a sensor signal which is a function of a parameter which changes depending on whether the clamp is closed; and
   means responsive to the sensor signal for providing an indication that the IV set should not be removed from the control device unless the sensor signal indicates that the clamp is closed.

10. The invention of claim 9 wherein the control device has a receptacle for receiving and holding a portion of the IV set when in operation, and wherein the means for providing an indication prevents removal of the IV set from the receptacle unless the sensor signal indicates that the clamp is closed.

11. The invention of claim 10 wherein the means for providing an indication comprises:
   a door for covering the receptacle when in a closed position and having an open position in which the portion of the IV set can be inserted into or removed from the receptacle; and
   means for maintaining the door in its closed position when the sensor signal indicates the clamp is open and releasing the door to permit it to be moved to its open position when the sensor signal indicates that the clamp is closed.

12. The invention of claim 9 wherein the means for providing a sensor signal comprises a flow sensor for sensing fluid flow through the IV set.

13. The invention of claim 9 wherein the means for providing a sensor signal comprises a pressure sensor for sensing fluid pressure in the IV set downstream from the portion of the IV set acted upon by the control device and upstream from the clamp.

14. The invention of claim 13 wherein the clamp, as it is closed, acts on the IV set to produce a fluid pressure increase which is sensed by the pressure sensor.

15. The invention of claim 9 and further comprising:
   means for providing a signal indicating an attempt to remove the IV set from the control device; and wherein the means for providing an indication provides a human perceivable warning based upon the sensor signal and the signal indicating an attempt.

* * * * *